US008481075B2

(12) United States Patent
Xiaoping et al.

(10) Patent No.: US 8,481,075 B2
(45) Date of Patent: Jul. 9, 2013

(54) PREPARATION AND APPLICATION OF BIODEGRADABLE-MATERIAL-MADE MICROSPHERE VASCULAR EMBOLUS CONTAINING LIPOSOME-ENCAPSULATED CYTOKINES

(75) Inventors: Li Xiaoping, Beijing (CN); Cui Heng, Beijing (CN); Wei Lihui, Beijing (CN); Feng Jie, Beijing (CN); Hong Hong, Beijing (CN); Li Xinjian, Beijing (CN); Qi Xianrong, Beijing (CN)

(73) Assignee: Beijing Shengyiyao Science & Technology Development Co. Ltd., Beijing (CN)

( * ) Notice: Subject to any disclaimer, the term of this patent is extended or adjusted under 35 U.S.C. 154(b) by 378 days.

(21) Appl. No.: 11/955,490

(22) Filed: Dec. 13, 2007

(65) Prior Publication Data

US 2009/0155344 A1    Jun. 18, 2009

(51) Int. Cl.
*A61K 9/127* (2006.01)
*A61K 31/00* (2006.01)
*A61K 47/36* (2006.01)
*A61P 35/00* (2006.01)

(52) U.S. Cl.
USPC ........... 424/450; 424/418; 424/422; 424/602; 514/19.2; 514/54

(58) Field of Classification Search
None
See application file for complete search history.

(56) References Cited

U.S. PATENT DOCUMENTS

| | | | | |
|---|---|---|---|---|
| 5,417,982 A | * | 5/1995 | Modi | 424/486 |
| 5,653,974 A | * | 8/1997 | Hung et al. | 424/85.1 |
| 2002/0147208 A1 | * | 10/2002 | Fleshner-Barak et al. | 514/283 |
| 2003/0211130 A1 | * | 11/2003 | Sanders et al. | 424/423 |
| 2006/0002966 A1 | * | 1/2006 | Pauletti et al. | 424/422 |
| 2008/0020052 A1 | * | 1/2008 | Li et al. | 424/490 |

FOREIGN PATENT DOCUMENTS

WO    WO 2006-029554    *  3/2006

OTHER PUBLICATIONS

Wakabayashi et al., Neurol. Med. Chir (Tokyo 37:739-746, 1997).*
Kibat et al (1990) "Enzymatically activated microencapsulated liposomes can provide pulsatile drug release" FASEB vol. 4.*
Dhoot and Wheatley 2003 "microencapsulated liposomes in controlled drug delivery: strategies to modulate drug release and eliminate the burst effect" J Pharm Sci 92(3):679-89.*
Http://www.cnki.net; 1994-2008 China Academic Journal Electronic Publishing House, 2 pages.
J Sichuan Univ (Med Sci Edi) vol. 35 No. 3, 2004, 1994-2007 China Academic Journal Electronic Publishing House, http://www.cnki.net, 3 pages.

* cited by examiner

*Primary Examiner* — Jeffrey Stucker
*Assistant Examiner* — Adam M Weidner
(74) *Attorney, Agent, or Firm* — Thomas Horstemeyer, LLP

(57) ABSTRACT

The present invention discloses preparation and application of a kind of biodegradable-material-made microsphere vascular embolus that contains liposome-encapsulated cytokines. The present invention is technologically characterized by encapsulation of liposome-wrapped immunocytokines such as IL-2, TNF and interferon by sodium polysaccharide or gelatin, which is extracted from natural alga and is good at biodegradability and biocompatibility. Owing to the encapsulation procedures, cytokine microspheres can take shape measuring 50-75 μm, 75-150 μm, 100-200 μm, 200-300 μm, 200-450 μm, 100-300 μm, 300-500 μm, 500-700 μm, and 700-900 μm. The microsphere preparations are good targeting medication for embolism treatment and immunochemotherapy of animals loaded with human hepatocarcinoma and cervical cancer, as well as human suffering from late-stage or recurrent liver cancer, renal tumors, bladder cancer, colon carcinoma and rectal cancer.

12 Claims, No Drawings

PREPARATION AND APPLICATION OF BIODEGRADABLE-MATERIAL-MADE MICROSPHERE VASCULAR EMBOLUS CONTAINING LIPOSOME-ENCAPSULATED CYTOKINES

FIELD

The present invention relates to a biodegradable-material-made microsphere vascular embolus, the preparation and application thereof, and particularly relates to microspheres that can take shape measuring 50-75 μm, 75-150 μm, 100-200 μm, 200-300 μm, 200-450 μm, 100-300 μm, 300-500 μm, 500-700 μm, and 700-900 μm by using sodium polysaccharide or gelatin with good biodegradability and biocompatibility and liposome-encapsulated cytokines which are extracted from natural alga. The microsphere preparations are good as a targeting medication for tumor arterial embolism and immunochemotherapy.

BACKGROUND

The therapy method of tumor arterial embolism is to inject an embolus into micro-arteries, causing mechanical blocking and inhibiting tumor growth. In 1981 Kato debuted this therapy method combining chemotherapeutic drugs with embolism materials for treating malignant tumors unsuitable for surgical operations. In recent years this method has been applied to treat hepatocarcinoma, renal cancer, tumors in pelvis and head and neck showing effective results. However, this method suffers from a high relapse rate.

Microsphere preparations are particles made by medications and proper auxiliary materials through micro-encapsulation technology. Effectiveness of a microsphere for embolism purposes depends on diameter, degrading speed of skeleton of the microsphere, drug-carrying speed, and drug release speed. The drug-containing microsphere preparations can block micro-vessels, which supported the carcinoma, and the embolism can supply anti-tumor drugs to tumor-targeted area and kill cancerous cells, which enables the drugs to be oriented and controllable. This kind of method for drug administration is able to improve drug distribution in vivo and pharmacokinetic features, increase bioavailability of drugs, improving treatment effect, and alleviate toxic or side effects.

Microsphere preparations for tumor arterial embolism should have characteristics as followings: powerful enough to embolism, strong mechanically and stable physically and chemically, the drug can be released slowly and persistently, maintaining a therapeutic concentration in the targeted areas; the drug carrier can be eroded by the receiver, and is biocompatible, free from immunogenicity, and free from harms to body even lingering around the targeted areas for a long time.

Sodium alginate is a sodium polysaccharide extracted from natural alga, forming sticky gel when solved in water. Under presence of calcium ion, its macromolecular chains can cross link and solidify. This kind of microsphere is a kind of biological derived materials having good biocompatibility. Accordingly, it can be processed to be a round solid microsphere with different sizes as desired. Under the phosphoric acid buffer condition in animal vessels, calcium ions seep out and the microspheres degrade in the form of molecular chains within 5-10 days or 3-6 months. The degradation products are mannitose and gulose being unable to be absorbed by the body. Size and evenness of the microspheres are controllable and fast bulging once they enter into vessels, let alone they are good at location. Thus sodium alginate is made as microspheres that wrap anti-tumor drugs and/or encapsulate liposome-wrapped cytokines, releasing the drugs/cytokines to specific organs on specific times for local immunochemotherapy of tumors after being administered to the target organs.

Immunotherapy can eradicate residual tumor cells and small metastatic micro-tissues and early-stage tumors, and prevent metastasis and relapse, acting as an effective auxiliary specific therapy. Cytokines play an important role in modulating immunity, fighting against infection and tumor.

Interleukin-2 (IL-2) is able to transform static pre-cytotoxic T cells to cytotoxic T cells, maintain growth of lymphokine-activated killer (LAK) cells and TIL cells, enhance non-specific killing of tumor cells via activated macrophages, and is produced in lymphokine-activated killer (LAK) cells. A combination of solo or infusion of killer cells can reduce metastasis and relapse of tumors. IFN-Γ is produced by a kind of activated T cell or by Natural Killer (NK) Cells, preventing a wide variety of tumor cells from propagating, enhancing immunogenicity of tumor cells and modulating cell-mediated immunity, including stimulating propagation of NK and monocyte, maintaining persistent TH1 type cell reaction, inducing production of IL-12, forming a cycle of positive feedback. TUMOR NECROSIS FACTOR is versatile fighting against tumors by taking cytotoxic effects onto some certain cells, causing necrosis of newborn vessels of tumor, and/or causing pathological blood coagulation via enhancing blood coagulation of endothelial cells of tumor vessels blocking blood supply to tumor tissues. In addition, TUMOR NECROSIS FACTOR can kill tumor cells by activating some hydrolase.

Lab and clinical researches reveal that cytokines such as interleukin-2 (IL-2), interferon (IFN-α, β and γ) and tumor necrosis factor (TNF) are able to fight against tumors, more effective when used in cohort. Cytokines and chemotherapeutic drugs can take synergistic effect or enhance therapeutic effect when they are used together. Research also reveal that TNF-α, IFN-α, IFN-γ, and IL-2, etc. can help tumors more sensitive to chemotherapeutic drugs.

Besides inducing differentiation of tumor cells, interferon also amplify sensitizing effects of amuycin (ADM), 5-FU, cisplatin, vincaleucoblastine, and alkylating agents. In practicing immunotherapy, IFN-α is often used in combination with IL-2, which is superior to using either of them exclusively, causing an effect of 1+1>2. A triple use of IFN-α, IL-2 and TNF-α can well assist chemotherapeutic drugs. Cytokines also modulate expression of multiple drug resistance gene (MDR1), enhancing cytotoxicity of MDR1-related amycin and vincristine, showing a time and concentration dependence. Highly concentrated cytokines can reverse MDR1 significantly, enhancing sensitivity to chemotherapy of tumor cells, improving micro-environment of tumors, and enhancing body's immunoresponse to tumor cells, owing to which the tumors can be contained. Thus cytokines combined with chemotherapy can be applied to chemotherapy-resistance tumors.

Some chemotherapeutic drugs such as CTX, MMC, ADM and DDP can help cytokines such as IL-2 more effective against tumors, taking synergistic effect or improving therapeutic effect. Along with chemotherapy, administration of immunotherapy can alleviate side effects of chemotherapy, improve host tolerance, increase tumor inhibition rate, reduce local relapse and far-reaching metastasis rate. On the other hand, immunotherapy can enhance the effect of chemotherapy. Therefore, it is reasonable to jointly use many ways to fight against tumors, and immunochemotherapy is an important way to treat tumors.

Professor Tadatsugu Taniguchi of Tokyo University of Japan recently published his research on a combined use of interferon and anti-tumor agents on Nature e-magazine, reporting that interferon can up level expression of P53 protein in cells. A combined use of interferon with radiotherapy or chemotherapy is superior to using chemotherapy or radiotherapy exclusively, helping to reduce dosage of anti-tumor agents and alleviate side effects. British Windbichler GH et al. conducted a prospective study (a randomized three-phase clinical trial) on 148 IC-IV phase primary ovary cancer patients who have undergone tumor-cell-number-dwindling operation, administering them a combination of interferon-Γ and CP. The author held that addition of interferon-Γ into first-line chemotherapeutic drugs is able to prolong progression-free survival cycle of tumors.

Owing to side effects of cytokines in vivo, application of the cytokines are limited. IL-2 has a short half-life and poor stability in vivo, and large dosage of IL-2 can compromise hepatic and renal functions and cause lung capillary leaking syndrome. TNF-α can be discharged by kidney and decomposed by some enzymes, having short half-life, being unstable in vivo, poorly tolerable by human beings. Side effects of TNF-α can be fever, nausea, vomiting, headache, even server hypotension and shock.

How to reasonably use cytokines is very meaningful. Current measures to properly use cytokines include: (1) jointly using various cytokines (IFN, IL-2) or using cytokines in combination with chemotherapeutic drugs in order to lower dosage of cytokines; (2) change structure of cytokines trying to obtain cytokines that are highly effective but less toxic, such as developing derivatives of TNF. (3) Using liposome capsule can significantly enhance stability and in vivo bioavailability of cytokines, elongate half-life, alleviate toxicity, target site more precisely, increase bioactivity, and improve anti-tumor and immunomodulation functions. (4) Change routes and approaches for administration of cytokines Arterial intervention is an important approach to treat solid organs. Drugs sent to a local site of tumor tissues via arterial embolism can directly distribute drugs to the tumor tissues, maintaining a high drug concentration locally, activating functions of effector cells, more powerful fighting against tumors. Localized immunotherapy can overcome immunosuppression caused by tumors, easily spark immune memory and immune response, and enjoy less systemic side effects and safer usage. Locally used IFN can help a high-concentration drug to directly contact tumor tissues, enhance infiltration of macrophages and lymphocytes into lesions and their surroundings, and strongly destroy tumor cells. For exposed tumors direct injection of IFN into body of papilloma, breast cancer or cervical cancer can achieve satisfactory short-range effect.

Gaojian et al. treated 62 HBsAg-positive hepatocarcinoma patients using a combination of IFN-α 1b with chemotherapy embolism via hepatic artery (TACE) observing therapeutic effect and prognosis. The results showed that a cohort of IFN+TACE can inhibit reproduction of hepatitis B virus, alleviate hurt to the liver caused by interventional chemotherapy, decrease in-liver relapse rate, increase survival rate and reduce side effect. Pan Tiejun et al. treated malignant renal tumors using embolism therapy with a cohort of TNF and IL-2, comparing results with patients receiving renal embolism exclusively. His results showed that tumor tissues injected with cytokines had much more infiltration of lymphocytes and macrophages, and ends of renal veins were stuffed with necrotic tumor cells, and no tumor cells survived under the masses. His results suggest that combined use of TNF and IL-2 on the one hand causes ischemia and death of tumor tissues by blocking blood supply to the tissues, and on the other hand activates macrophages, recognizing and killing tumor cells and reducing inducing of drug resistance for targeted cells. Cao Zeyi et al. observed activity of TIL and NK by irrigating IL-2 via pelvic retroperitoneal space, probing the feasibility of biotherapy. His results showed that the cohort IL-2+5-FU is different from either solo 5-FU or solo IL-2 in CD3, CD4, CD8, CD25 and NK, indicating irrigating IL-2 via pelvic retroperitoneal space can activate TIL and NK of tumor tissues.

Microsphere preparations are made with certain drugs and auxiliary materials using micro-encapsulation technology. Administration of drugs in the form of a microsphere helps the drugs be site targeted and release controllable. This kind of method for drug administration is able to improve drug distribution in vivo and pharmacokinetic features, increase bioavailability of drugs, improving treatment effect, and alleviate toxic or side effects. Chemotherapeutic-drug-containing microspheres via arterial embolism can cluster in arterial vessels around the lesion blocking blood supply to the lesion and releasing drug persistently, effectively inducing apoptosis and causing ischemic and anoxia and death of cancerous cells.

SUMMARY

One objective of the present disclosure is to provide a kind of biodegradable-material-made microsphere vascular chemotherapy embolus that contains liposome-encapsulated cytokines (IL-2, TN F, interferon).

Another objective of the present disclosure is to provide a method for preparing the said kind of microsphere vascular chemotherapy embolus that contains liposome-encapsulated cytokines (IL-2, TNF, interferon).

Yet another objective of the present disclosure is to use the said microsphere vascular embolus to treat animals loaded with human hepatocarcinoma and cervical cancer, as well as human suffering from late-stage or recurrent hepatocarcinoma, renal tumors, bladder cancer, colon carcinoma and rectal cancer.

The present invention discloses preparation and application of a kind of biodegradable-material-made microsphere vascular embolus that contains liposome-encapsulated cytokines. The present invention is technologically characterized by encapsulation of liposome-wrapped immunocytokines such as IL-2, TNF and interferon by sodium polysaccharide or gelatin, which is extracted from natural alga and is good at biodegradability and biocompatibility. Owing to the encapsulation procedures, cytokine microspheres can take shape measuring 50-1000 µm, 50-75 µm, 75-150 µm, 100-200 µm, 200-300 µm, 200-450 µm, 100-300 µm, 300-500 µm, 500-700 µm, and 700-900 µm. The microsphere preparations are good targeting medication for embolism treatment and immunochemotherapy of animals loaded with human hepatocarcinoma and cervical cancer, as well as human suffering from late-stage or recurrent liver cancer, renal tumors, bladder cancer, colon cancer and rectal cancer.

Embodiments of the present disclosure achieves its goals using technological means as below:

A kind of biodegradable-material-made microsphere vascular embolus that contains liposome-encapsulated cytokines, wherein the embolus contains drug carrier and liposome-encapsulated cytokines, said carrier contains the said liposome-encapsulated cytokines.

The drug carrier is sodium alginate or gelatin.

The liposome-encapsulated cytokines are encapsulated by lipid dual-layer forming microspheres with a size in the range of 25 nm-5 µm, with a size of 1 µm in general.

The liposome can be Phosphatidyl choline (lecithin, PC), phosphatidylserine in cow brain, phosphatidyl inositol, or dipalmitoyl-DL-α-phosphatidylcholine. To increase encapsulation rate, stearamide phosphate (10%) can be added, and in order to make the membrane more stable, cholesterol (20-50%) can be added. The liposome can be made using a film dispensing method, an ultrasound method, an ethanol irrigation method, a reversal steaming method, or a freeze dry method.

The ratio of weight of said sodium alginate or gelatin to the weight of said liposome-encapsulated cytokines in the range of 1:1 to 90:1.

The sodium alginate or gelatin microsphere vascular embolus that contains liposome-encapsulated cytokines can be microspheres or micro-gel-bead stored in bivalent-metal-cation solidifying liquid.

The sodium alginate or gelatin microsphere vascular embolus that contains liposome-encapsulated cytokines can also be powder-like particles.

The micro-gel-bead or microsphere stored in the solidifying liquid has a diameter in the range of 50 to 900 µm.

The powder-like particle has a diameter in the range of 50 to 900 µm.

A method for preparing a kind of sodium alginate microsphere vascular embolus that contains liposome-encapsulated cytokines, wherein the preparation procedures are as below:
(1) Weigh the liposome-encapsulated cytokines according to the proportion and dissolve obtaining a liposome-encapsulated cytokines solution;
(2) Weigh sodium alginate according to the proportion and dissolve obtaining a sodium alginate solution;
(3) Weigh calcium chloride solution or barium chloride and prepare a solidifying solutions with a concentration in a range of 1 to 10%;
(4) Mix liposome-encapsulated cytokines solution with sodium alginate solution, and drip the mixture liquid through a high-pressure-static-charge microsphere-generation device into the said solidifying solution forming round or ovary microsphere or micro-gel-bead that contains liposome-encapsulated cytokines, obtaining liposome-encapsulated cytokines solution.

The solvents can be water, ethanol, acetic acid or hydrate of sodium.

The high-pressure-static-charge microsphere-generation device is a static charge generation instrument, which has positive and negative poles. The positive pole is connected with needle of a micro-injection device, and the negative pole is linked to a stainless ring soaked in the solidifying solution. The injection device contains a mixture of liposome-encapsulated cytokines and sodium alginate that is dripped into said solidifying solution forming microsphere.

If the microsphere embolus is stored in the solidifying liquid, it is called wet microsphere whose diameter is in a range of 100 to 200 µm.

When the liquid is drained and the microsphere is placed into a baking oven for dry, seal and store, a kind of powder-like particle can be obtained called dry microsphere whose diameter is in a range of 100 to 200 µm.

A method for preparing biodegradable-material-made microsphere vascular embolus that contains liposome-encapsulated cytokines, wherein the detailed procedures are as below:
(1) Weigh the liposome-encapsulated cytokines according to the proportion and solve using certain solvents obtaining liposome-encapsulated cytokines solution;
(2) Weigh gelatin according to the proportion and dissolve using water under heating, obtaining a gelatin solution;
(3) Mix liposome-encapsulated cytokines solution with gelatin solution, stir even, pour the mixture into 55-60° C. mineral oil, stir and cool to below 5° C., obtaining a wet gelatin microsphere embolus that contains liposome-encapsulated cytokines;
(4) Add isopropanol or acetone to the wet gelatin microsphere to conduct dehydration, stir and isolate microsphere, wash the microsphere using isopropanol for two times, allow to dry;
(5) Take some microspheres, add 10% aldehyde isopropanol solution, solidify, filter, and dry, obtaining dry gelatin microspheres.

Said solvent involved in step (1) can be water, ethanol, acid such as acetic acid or alkali such as caustic alkali.

DETAILED DESCRIPTION

Clinical Application

Guided by interventional ultrasound or interventional radiation, insert a catheter into an artery that supplies blood to the target organ conducing arteriography on which depend to select the diameter of microsphere embolism. The embolism procedures should be conducted using a micro-catheter as much as possible and sterile operations should be obeyed. Uncap the bottle and allow to stand for settlement, inspire the solidifying solution in the bottle using a syringe and add equal portion of normal saline (NS) to rinse the microsphere for three times, or inspire the preservation solution (solidifying solution) in the bottle using a syringe and add an equal portion of NS, and transfer the mixture to a sterile bowl, rinse the microspheres with 50-60 ml of NS once and discard the NS, then add certain amount of diluted contrast medium and mix evenly (enabling microsphere to sufficiently suspend in the contrast medium). Under fluoroscopy guide, irrigate the mixture slowly, or in several portions (precautions to over much embolism), until the contrast medium significantly lowers its speed completing embolism. Repeat the arteriography determining embolism effect.

In case the embolus preparation is in the form of powder-like particle, solve the dry microsphere contained in sealed containers using NS (wet microsphere), and add certain amount of diluted contrast medium and mix even (enabling microsphere to sufficiently suspend in the contrast medium). Under fluoroscopy guide, irrigate the mixture slowly, or in several portions (precautions to over much embolism), until the contrast medium significantly lowers its speed completing embolism. Repeat the arteriography determining embolism effect.

In one embodiment, the biodegradable-material-made acting as drug carrier is a natural extract collected from natural plant brown alga. The biodegradable-material-made is a sodium polysaccharide that contains β-D-mannitol and α-L-gulose. It is a linear macromolecule that has a molecular weight in the range of 50,000 to 100,000 Dalton, very powerful in combining water, forming a sticky gel when solved in water. Under presence of calcium ion, its macromolecular chains can cross link and solidify being able to be processed as round or ovary wet or solid microsphere with different sizes. This kind of microsphere is good at biocompatibility. In body of creatures, calcium ions seep out and the microspheres degrade without causing debris and toxic effect within 3-6 months in the form of falling out of chains. The microspheres can cause perpetual embolism (when the embolus stays in the blood vessel as long as 2 months, thrombosis in blood vessels of patients take place perpetually blocking the blood vessels) of blood vessels of targeting organs achieving therapeutic goals. The gelatin takes similar effects.

In practical operation, the "biologically multifunction microsphere" physically block small arteries supplying blood to the tumors or arteries around the tissues cutting off blood and nutrient supply causing ischemia, anoxia, atrophy and necrosis. Dwindling blood supply to targeted organs also facilitates surgical operations. As an anti-tumor drug carrier, the microspheres can slowly release drugs to specific site on specific time, significantly improving therapeutic effect, alleviating side or toxic effects of the drugs, and taking double effects of both embolism and chemotherapy.

One embodiment, among others, uses some liposome-encapsulated cytokines to treat cancers and applies semi-crosslink structure and degradability of the microsphere, considering empirical usage of embolus made of biodegradable materials, and the advantages such as high safety, free from toxicity, free from immunogenicity, free from genetic toxicity, free from reproductive toxicity and free from carcinogenicity. Usage of bio-degradable materials acting as drug carrier to carry anti-tumor drugs can help send drugs to specific site on specific time, killing tumor cells and achieving therapy goal.

Immunotherapy can eradicate residual tumor cells and small metastatic micro-lesions, and prevent metastasis and relapse, in which cytokines act as important constituents, interacting to induce a wide variety of cytokines participating modulation in the immune network. Drugs sent to local site of tumor can directly target the tumor tissues, maintaining a high drug concentration locally, activating functions of effector cells, more powerful fighting against tumors; localized immunotherapy can overcome immunosuppression caused by tumors; easily spark immunological memory and immunoresponse; enjoy less systemic side effects and safer usage.

Cytokines and chemotherapeutic drugs can take synergistic effect or enhance therapeutic and radiotherapy effect when they are used together, moreover combination of various cytokines is more effective than using of a solo cytokine. Localized administration of immunotherapy can alleviate immunosuppression and side effects of chemotherapy, improve host tolerance, increase tumor inhibition rate, and reduce local relapse and far-reaching metastasis rate.

Administration of local immunotherapy via arteries is of great importance. However, there are few data available on results of a combined use of cytokine-contained microsphere and anti-tumor-agent-contained microsphere. One embodiment uses sodium alginate or gelatin to prepare microsphere that contains liposome-encapsulated cytokines, hoping the drug-contained microsphere can release drug to specific site on specific time once it is irrigated to certain target organs with purpose of local immunochemotherapy of tumors. The microsphere preparations can take multiple effects such as arterial embolism, chemotherapy, and immunotherapy, enhancing therapeutic effect, reducing relapse, especially when they are applied to hepatocarcinoma and renal cancer.

One embodiment, among others, can be further described by the following embodiments, which is used in a descriptive sense only and not for purpose of limitation.

Preparation of Liposome-encapsulated Cytokine IL-2

1. Materials and Methods (Reverse Steaming Method)

Film-making material: soybean phosphatidylcholine (SYPC):cholesterol=1:1 (mol ratio), the organic phase is prepared with ether.

Water phase: IL-2 0.1M PBS, organic phase:water phase=3:1, solve the film-making material in 30 ml of ether, add IL-2 solution, during interval of icy bath vibrate the mixture using ultrasound for 2-3 min (the interval is 0.5 min long), making even emulsion, remove ether via 20-25 degree rotation steaming, obtaining white even liposome suspension.

2. Determination of Encapsulation Rate

Centrifuge the liposome suspension at high speed and low temperature (30000 G, 60 min, 4° C.), collect supernatant, rinse using PBS, centrifugate again, and repeat twice, add ether to lower layer that contains liposome separating water phase and fatty phase, determine concentration of IL-2 in the water phase using Lorry method, calculating encapsulation rate. The encapsulation rate should be 34.5+1.12%. Repeat the above for five times for conducting recovery rate experiment. The recovery rate is 95% on average (determine concentration of protein in the primary solution using ultraviolet spectrophotometry, BCA protein concentration determination and Lowry method respectively).

$$\text{Encapsulation rate }(\%) = \frac{\text{content of drug encapsulated in the liposome (mg)}}{\text{total drug added (mg)}} \times 100\%$$

$$\text{Recovery rate }(\%) = \frac{\text{encapsulated drug (mg/ml)} + \text{free drug (mg/ml)}}{\text{drug content in the un-contrifugated sample (mg/ml)}} \times 100\%$$

3. Observation Using Electron Microscope

Dilute the liposome solution certain times and transfer it to a piece of copper web, dry using a piece of filter paper, allow to stand for 10 min, negatively stain using 5% phosphotungstic acid for several minutes, allow to dry naturally, conduct electron observation.

Prepared IL-2 liposome is a suspension, after negatively stained using phosphotungstic acid, most liposome becomes big mono-layer liposome with a diameter of 0.2 um.

4. Stability experiment: take liposome and determine encapsulation amount of the same day, and store under 4° C., take sample for centrifugation at the second, forth and sixth month and determine encapsulation amount. Again take 1 ml of liposome solution and dilute one time and store under 4° C., determine encapsulation amount at the fourth month, and calculate leaking rate.

$$\text{Leaking rate} = \frac{\text{encapsulation amount of the prepared sample on the current day} - \text{encapsulation amount of a certain time}}{\text{encapsulation amount of the prepared sample on the current day}} \times 100$$

The leaking rate determination reveals that undiluted liposome sample did not change significantly in leaking rate as long as six months stored under 4° C., in contrast, the sample diluted by one fold significantly increased leaking rate by 23% stored for four months under 4° C.

5. Determination of Activity (ConA-induced T Cell Number Determination)

(1) Transfer liposome that encapsulates IL-2 to RPMI-1640 CTLL cell culture, take cells that grow in logarithm, 250 G, 10 min, wash out residual IL-2. Stain using trypan blue stain and count cell number determining cell activity. Suspense cells to a concentration of $1\times10^5$/ml using RPMI-1640 culture liquid that contains 10% bovine serum, and pipet 0.1 ml of doubling diluted standard IL-2 solution or sample into the 96-well plate, with each dilute degree filling into 3 wells. There are 8-10 dilute degrees in total. Do not add PBS to negative control. Add 0.1 ml of cell suspension into each well and cultivate the plate in a 5% CO2 incubator under 37° C. for 18-24 h. add 10 μl of deoxidate thymidine $(1.85\times10^4Bq)[H^3]$deoxythymidine and continuously cultivate for 4 h. Collect cells to a piece of glass fiber filter paper using a multi-head cell collector. Rinse the filter for 3 times using water solution of 3% acetic acid removing free $[H^3]$deoxythymidine. Transfer the filter paper into a liquid γ-counter. Add 5 ml of scintillation liquid and conduct isotope count using scintillometer. Plot a chart for the sample according to CPM values and calculate concentration of IL-2 for the sample to be tested.

(2) Grind C57BL/6 mouse spleen to $5\times10^5$/ml single cell suspension, add ConA 5 μg/ml, cultivate in a 5% CO2 culture box for 40-48 h under 37° C. Place the culture liquid onto lymphocyte stratification liquid, and centrifugate at 1,700 r/min for 15 min. Take cells on the interface layer. Prepare above reactive cells $1\times10^3$/ml suspension. Divide the 96 wells into 3 groups (blank group, control group, sample group) with each group taking up 10 wells. Add 0.1 ml of cell suspension into each well. Into wells of the blank group add PBS of the same volume, and to wells of the control group add 0.1 ml doubling diluted standard IL-2 solution, and to wells of the sample group add 0.1 ml of IL-2 liposome (100 unit of IL-2). Cultivate the plate in a 5% $CO_2$ incubator for 40-48 h under 37° C. Collect cells to a piece of glass fiber filter paper using a multi-head cell collector and conduct isotope count using scintillometer. The results showed that the active count for the blank group is 3411+358, for the control group is 16540+1987, for the sample group is 21003+1812. Encapsulated IL-2 liposome is superior to the un-encapsulated in the isotope count.

II. Preparation of Liposome-encapsulated Cytokine IFN

1. Materials and Methods

Soybean phosphatidylcholine (SYPC):cholesterol=2:1 (mole ratio), the organic phase is prepared with chloroform. Water phase: IFN-α 0.1M PBS.

2. Preparation Method (Reverse Steaming Method)

Lecithin 40 mg, cholesterol 20 mg, solve them in 4 ml of chloroform, 40° C., water batch, remove chloroform using 100-150 rpm rotation steam, add the solution to 4 ml of ether, and add IFN-α solution (0.5 ml of PBS) and mix. During interval of icy bath vibrate the mixture using ultrasound for 2-3 min (the interval is 0.5 min long), making even emulsion. Finally remove un-encapsulated drug using gel-column chromatography.

3. Determination of Diameter of Particle

Dilute the liposome-encapsulated IFN-α, dilute using NS, transfer it to a piece of copper web, dry using a piece of filter paper, allow to stand for 10 min, negatively stain using 5% phosphotungstic acid for several minutes, allow to dry naturally, conduct electron observation determining diameter of particle.

4. Determination of Encapsulation Rate

Centrifugate the liposome suspension at high speed and low temperature (30000 G, 60 min, 4° C.), collect supernatant, allow for settlement, rinse using PBS, centrifugate again, repeat twice, add ether to lower layer that contains liposome separating water phase and fatty phase, determine concentration of IFN-α in the water phase using Lorry method, calculating encapsulation rate. The encapsulation rate should be 34.5+1.12%. Repeat the above for five times for conducting recovery rate experiment. The recovery rate is 95% on average.

5. Stability experiment: take liposome and determine encapsulation amount of the same day, and store under 4° C., take sample for centrifugation at the second, forth and sixth month and determine encapsulation amount. Again take 1 ml of liposome solution and dilute one time and store under 4° C., determine encapsulation amount at the fourth month, and calculate leaking rate.

$$\text{Leaking rate} = \frac{\text{encapsulation amount of the prepared sample on the current day} - \text{encapsulation amount of a certain time}}{\text{encapsulation amount of the prepared sample on the current day}} \times 100$$

The leaking rate determination reveals that undiluted liposome sample did not change significantly in leaking rate as long as six months stored under 4° C., in contrast, the sample diluted by one fold significantly increased leaking rate by 23% stored for four months under 4° C.

6. Determination of Activity (Crystal Violet Stain Method Based on Cytopathic Effect (CPE))

Dilute VSV in the proportion of 1:200 using 10% bovine serum-containing MEM culture solution, inoculate the dilute for propagation to single layer Wish cells that in logarithmic growth. Cultivate until CPE is as high as 75-100% and frozen reserved at −20° C. On the next day repeat freezing and melting for 2-3 times and collect VDV strain in liquid nitrogen. Determination of titer potency of VSV: at the 24th hour, dilute degree of wells in which half of cells present CPE is determined as one $TCID_{50}$. Multiply reciprocal value of this dilute by ten times obtaining viral potency ($TCID_{50}$/ml). Micro-determination of CPE: China Bioproduct Rules requires that detection of interferon's protection effect on Wish cell should use Wish cell/VSV system, and record protection potency using a five-rank scoring method depending on CPE extent, and national standard product (LOT03-94) should be referred when labeling IU value.

Crystal Violet Stain Method:

Prepare well developed mono-layer Wish cells a $5\times10^5$ cells/ml suspension using 10% bovine serum-containing MEM culture solution. Inoculate the suspension to a 96-well plate filling 100 μl into each well. At the same time set standard sample control that has the same volume as that of the sample. Cultivate the plate in a 5% $CO_2$ incubator at 37° C. for 4 h. Into each well as 4-time gradually diluted interferon sample filling 100 μl into each well. Dilution of the sample is with 7% bovine serum-containing MEM culture liquid, cultivate in a incubator at 37° C. for 18-24 h, discard supernatant and attack the Wish cells using VSV ($100TCID_{50}$/ml) that are cultivated and diluted by 3% bovine serum-containing MEM culture liquid, cultivate the attacked cells in a 5% $CO_2$ incubator at 37° C. for 24 h. Discard the supernatant, add 4011 crystal violet to each well staining for 30 min at room temperature, discard stain liquid, remove residual stain liquid using distilled water, absorb the wells dry and add 100 μl of decolourant liquid into each well for decoloration. Test OD value of each well at 570 nm using SPECTRA 250 automatic microplate reader. Calculate potency value of the sample on the automatic reader using national standard sample of IFN-α.

III. Preparation of Sodium Alginate Microsphere that Contains Encapsulated-cytokines
1. Materials and Methods
2. Encapsulation Rate
3. Stability
4. Release Amount IV. Establishment and Usage of Rabbit Model of Hepatocarcinoma
(1) Subject: 50 purely blooded clean New Zealand rabbits (provided by Experiment Animal Center of Chongqing Medical University), uneven in genders, aged 3-4 months, body weight 2-3 kg.
(2) Materials: Rabbits having subcutaneous Vx2 transplantation carcinoma are provided by Ultrasound Bioengineering Institute of Beijing Medical University. Bcl 2, bax immunohistochemistry stain kits are purchased from Boster, and VEGF immunohistochemistry stain kits are purchased from NeoMarker. DAB developing kits and slide gluing agents are purchased from Maxim, and catheter for hepatic artery and catheter perfusion from BD company.
(3) Method: slice fish-like tissue rampantly growing part on the edge of the lesion of Vx2 transplantation carcinoma into 3 masses measuring 1-2 mm. Plant the masses into left anterior lobe of liver. Two weeks later a cancerous lesion with a diameter 1 cm and grows in the form of infiltration takes place. At this time, puncture and insert and fix the intubation on the root of hepatic artery. The animals are randomized into 5 groups (10 animals in one group) using random digit table method: negative control group (receiving NS), positive control group (receiving cisplatin 1.28 mg/kg·d), experiment group 1 ($As_2O_3$ 0.6 mg/kg·d), experiment group 2 ($As_2O_3$ 1.2 mg/kg·d) and experiment group 3 ($As_2O_3$ 1.96 mg/kg·d). Administer the rabbits drugs obtained from the Embodiment 1 for consecutive 7 days. Five weeks later after planting the cancerous mass, cut normal hepatic tissue near the tumor and full cancerous tissue, weighing tumor weight, take one slide for both optical microscopy and electron microscopy from the cancerous tissue (the same site as before planting, within 15 cm) and normal tissue respectively.
(4) Observatory Parameters:
Tumor weight and average rate for inhibition of tumor weight for the positive control group and experiment group: Average rate for inhibition of tumor weight=(1−average tumor weight of group receiving drug/average tumor weight of negative control group)×100%. Observation using transmission electron microscope: tumor cells, cell volume of hepatic cells, morphology of nuclear and changes of nuclear chromatin. Examination of expression of bcl 2 bax genes, and expression of VEGF, in which the stain result is used to determine standard expression of bcl 2 bax genes; cells whose plasma or membrane stained brown-yellow are determined positive cells. Positive cells <5% is judged (−), 5-15% (+), 15-50% (++), >50% (+++). As for determining expression of VEGF, when newborn endothelial cells of capillaries, part tumor cell plasma and/or membrane are stained brown, they are judged positive. The cells that are explicitly stained are VEGF positive and those inexplicitly stained or free from being stained are judged VEGF negative.
(5) Statistic method: data collected are expressed in the form of x±s, and SAS 8.1 is used to conduct q test, Fisher's exact test. Treat the nude mouse loaded with human hepatocarcinoma by immunotherapy via arteries embolism.

V. Establishment of Model of Mouse Suffering from U14 Transplantation Cervical Cancer
1. Dilute U14 cervical cancer cells to $7 \times 10^6$ cancer cells/ml. Disinfect armpit area of right anterial lime of 34 NIH mice that weigh 18-22 g. Inject the suspension of said cancer cells subcutaneously at a dosage of 0.1 ml/each mouse ($7 \times 10^5$ cancer cells/each mouse). After the mice grow for 3-4 weeks with the cancer cells, remove the transplantation tumor mass slicing it dices measuring 1 mm×1 mm×1 mm, and again inoculate the dices under capsule of left lobe of liver of the mice.
2. Treatment of Nude Mouse Loaded with Human Hepatocarcinoma
Ten days later after having inoculated the tumor mass, open the original cut measuring longest and shortest diameter of lesion of the transplantation tumor under surgical microscope, as well as irrigate drug via intubation to hepatic artery. The animals are randomized into: A. NS group; B. IL-2 group; C. IL-2 liposome group; D. Exclusive chemotherapy group; E. IL-2+chemotherapy group; F. IL-2 liposome group+chemotherapy group.

Two weeks later measure six animals of each group, obtaining the longest and shortest diameter of lesion of the transplantation tumor. Calculate tumor volume and compare tumor growth rate (in which tumor volume growth rate is quotient of dividing post-treatment tumor volume by pre-treatment tumor volume). Conduct HE stain to observe necrosis degree of the tumor (mild: 0-30%; moderate: 30-70%; severe: 71-100%), and to observe infiltration of lymphocytes, and natural survival time of rats loaded with tumor after treatment.

VI. Embolism of Hepatic Artery for Rats Suffering from Transportation Hepatocarcinoma
a) Establishment of Rat Transportation Hepatocarcinoma Model
Take 0.5-1 ml of cancerous ascites from abdomen of Wistar rats after they have been inoculated Walker-256 tumor cells for 3-5 days. Inject the ascites with sterile procedures under skin of healthy rats. 7-10 days later a tumor mass measuring 1-2 cm takes place. Take some fresh fish-like cancerous mass slicing it to dices as big as 1 $m^3$ and inoculating it to left lateral lobe of liver of rats. One week later hepatocarcinoma model that has a cancerous mass with a diameter of 0.5-1 cm takes place. Take 30 liver cancer model rats and irrigate embolus preparation via gastroduodenal and hepatic proper artery using PE-50 catheter under surgical microscope, owing to which the hepatic artery can be blocked. Together with irrigation of the drug transiently block common hepatic artery and right branch of proper hepatic artery. Having irrigated the drug, close the abdomen and raise the rats in the cages.
b) Hepatic Arterial Embolism
The animals are randomized into: A. NS group; B. IL-2 group; C. IL-2 liposome group; D. Exclusive chemotherapy group; E. IL-2+chemotherapy group; F. IL-2 liposome group+chemotherapy group.

The invention claimed is:
1. A composition consisting of:
a liposome encapsulating one or more cytokines, wherein said liposome is further encapsulated by a microsphere, said microsphere consisting of an alginate-bivalent cation complex and having a diameter in the range of 50-1000 microns.
2. The composition of claim 1, wherein said liposome is comprised of phosphatidyl choline, phosphatidylserine, phosphatidyl inositol, dipalmitoyl-DL-α-phosphatidylcholine, or any combination thereof.
3. The composition of claim 1, wherein said cytokine encapsulated by the liposome is selected from the group consisting of interleukin-2, tumor necrosis factor, interferon, and combinations thereof.

4. The composition of claim 1, wherein the weight ratio of the microsphere to said liposome-encapsulated cytokine is in the range of 1:1 to 90:1.

5. The composition of claim 1, wherein said composition is stored in a bivalent-metal-cation solidifying solution.

6. A method for preparing a composition consisting of a liposome encapsulating a cytokine, wherein said liposome is further encapsulated by a microsphere, comprising the steps of:

preparing a suspension of liposomes, wherein said liposomes encapsulate a cytokine;

preparing a solution comprising sodium alginate;

preparing a bivalent-metal-cation solidifying solution;

mixing said suspension of liposomes with said sodium alginate solution; and dripping said mixture through a high-pressure-static-charge microsphere-generation device into said bivalent-metal-cation solidifying solution thereby forming a population of liposomes, wherein each liposome of the population is encapsulated by a microsphere, each microsphere consisting of an alginate-bivalent cation complex and having a diameter in the range of 50-1000 microns.

7. The method of claim 6, wherein the weight ratio of said sodium alginate to said liposome-encapsulated cytokine is in the range of 1:1 to 90:1.

8. The method of claim 6, wherein said bivalent-metal-cation solidifying solution comprises barium chloride with a concentration in the range of 1 to 10%.

9. The method of claim 6, wherein said bivalent-metal-cation solidifying solution is a calcium chloride solution with a concentration in the range of 1 to 10%.

10. The method of claim 6, wherein said high-pressure-static-charge microsphere-generation device is a static charge generation instrument having positive and negative poles, said positive pole connected with a needle of a micro-injection device, and said negative pole linked to a stainless ring soaked in the bivalent-metal-cation solidifying solution, said micro-injection device including said mixture.

11. A method for treating an animal with human hepatocarcinoma or cervical cancer comprising administering a composition comprising a population of liposomes encapsulating a cytokine, wherein each liposome is individually encapsulated by a microsphere, each microsphere consisting of an alginate-bivalent cation complex, and wherein each microsphere has a diameter in the range of 50-1000 microns to an arterial blood vessel delivering blood to a tumor or a cancerous organ, whereupon the population of microsphere-encapsulated liposomes generates a vascular embolism, thereby reducing blood flow to the tumor or cancer.

12. A method for treating a human suffering from liver cancer, renal tumors, bladder cancer, colon carcinoma or rectal cancer comprising administering a composition comprising a population of liposomes encapsulating a cytokine, wherein each liposome is individually encapsulated by a microsphere, each microsphere consisting of an alginate-bivalent cation complex, and wherein each microsphere has a diameter in the range of 50-1000 microns to an arterial blood vessel delivering blood to a tumor or a cancerous organ, whereupon the population of microsphere-encapsulated liposomes generates a vascular embolism, thereby reducing blood flow to the tumor or cancer.

* * * * *